United States Patent [19]

Bodenmüller et al.

[11] Patent Number: 5,346,813
[45] Date of Patent: Sep. 13, 1994

[54] METHOD OF SCREENING FOR SMALL CELL LUNG CARCINOMA

[75] Inventors: Heinz Bodenmüller; Andreas Dessauer, both of Tutzing, Fed. Rep. of Germany

[73] Assignee: Boehringer Mannheim GmbH, Mannheim, Fed. Rep. of Germany

[21] Appl. No.: 982,112

[22] Filed: Nov. 25, 1992

Related U.S. Application Data

[63] Continuation of Ser. No. 617,102, Nov. 19, 1990, abandoned.

[30] Foreign Application Priority Data

Dec. 5, 1989 [DE] Fed. Rep. of Germany ....... 3940209

[51] Int. Cl.$^5$ .................... G01N 33/574; G01N 33/53
[52] U.S. Cl. .................................. 435/7.23; 435/7.2; 436/512; 436/63; 436/64; 436/813
[58] Field of Search ............... 435/7/23, 7.2; 436/512, 436/63, 64, 813, 815; 530/387.7, 388.24, 388.85, 389.2

[56] References Cited

FOREIGN PATENT DOCUMENTS 8807551 10/1988 PCT Int'l Appl. .

OTHER PUBLICATIONS

*Path. Res. Pract.,* vol. 183, 1988, pp. 412–417, Kayser et al., Expression of neuroendoctrine markers (neuron-specific enolase, synaptophysin and bombesin) in carainoma of the lung.
*The Embo Journal,* vol. 6, No. 11, 1987, pp. 3261–3268; R. E. Leube et Synaptophysin: molecular organization and mRNA expression as determined from cloned cDNA.
Südhof, T., *Nucleic Acids Research,* vol. 15, No. 22 (1987) 9607.
Südhof, T., *Science,* vol. 232 (1987) 1142–1144.

*Primary Examiner*—Toni R. Scheiner
*Attorney, Agent, or Firm*—Nikaido, Marmelstein, Murray & Oram

[57] ABSTRACT

In order to detect a small cell lung carcinoma, synaptophysin, its oligomers and/or its fragments are determined in body fluids.

23 Claims, No Drawings

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1930 base pairs
        ( B ) TYPE: nucleic acid
        ( C ) STRANDEDNESS: double
        ( D ) TOPOLOGY: linear ( i i ) MOLECULE TYPE: protein ( i x ) FEATURE:
        ( A ) NAME/KEY: CDS
        ( B ) LOCATION: 10..933

( x i ) SEQUENCE DESCRIPTION: SEQ ID NO: 1:

```
GCAGCAGCA ATG GAC GTG GTG AAT CAG CTG GTG GCT GGG GGT CAG TTC           48
          Met Asp Val Val Asn Gln Leu Val Ala Gly Gly Gln Phe
          1               5                   10

CGG GTG GTC AAG GAG CCC CTT GGC TTC GTG AAG GTG CTG CAG TGG GTC          96
Arg Val Val Lys Glu Pro Leu Gly Phe Val Lys Val Leu Gln Trp Val
    15              20                  25

TTT GCC ATC TTC GCC TTT GCT ACG TGT GGC AGC TAC ACC GGG GAG CTT         144
Phe Ala Ile Phe Ala Phe Ala Thr Cys Gly Ser Tyr Thr Gly Glu Leu
30                  35                  40                  45

CGG CTG AGC GTG GAG TGT GCC AAC AAG ACG GAG AGT GCC CTC AAC ATC         192
Arg Leu Ser Val Glu Cys Ala Asn Lys Thr Glu Ser Ala Leu Asn Ile
                50                  55                  60

GAA GTT GAA TTC GAG TAC CCC TTC AGG CTG CAC CAA GTG TAC TTT GAT         240
Glu Val Glu Phe Glu Tyr Pro Phe Arg Leu His Gln Val Tyr Phe Asp
```

|  |  |  |  |  |  |  |  |  |  |  |  |  |  |  |  |
|---|---|---|---|---|---|---|---|---|---|---|---|---|---|---|---|
| GCA | CCC | TCC | TGC | GTC | AAA | GGG | GGC | ACT | ACC | AAG | ATC | TTC | CTG | GTT | GGG |
| Ala | Pro | Ser | Cys | Val | Lys | Gly | Gly | Thr | Thr | Lys | Ile | Phe | Leu | Val | Gly |
|  |  | 80 |  |  |  |  | 85 |  |  |  |  |  | 90 |  |  |

288

| GAC | TAC | TCC | TCG | TCG | GCT | GAA | TTC | TTT | GTC | ACC | GTG | GCT | GTG | TTT | GCC |
|---|---|---|---|---|---|---|---|---|---|---|---|---|---|---|---|
| Asp | Tyr | Ser | Ser | Ser | Ala | Glu | Phe | Phe | Val | Thr | Val | Ala | Val | Phe | Ala |
|  | 95 |  |  |  |  | 100 |  |  |  |  | 105 |  |  |  |  |

336

| TTC | CTC | TAC | TCC | ATG | GGG | GCC | CTG | GCC | ACC | TAC | ATC | TTC | CTG | CAG | AAC |
|---|---|---|---|---|---|---|---|---|---|---|---|---|---|---|---|
| Phe | Leu | Tyr | Ser | Met | Gly | Ala | Leu | Ala | Thr | Tyr | Ile | Phe | Leu | Gln | Asn |
| 110 |  |  |  | 115 |  |  |  |  | 120 |  |  |  |  |  | 125 |

384

| AAG | TAC | CGA | GAG | AAC | AAC | AAA | GGG | CCT | ATG | ATG | GAC | TTT | CTG | GCT | ACA |
|---|---|---|---|---|---|---|---|---|---|---|---|---|---|---|---|
| Lys | Tyr | Arg | Glu | Asn | Asn | Lys | Gly | Pro | Met | Met | Asp | Phe | Leu | Ala | Thr |
|  |  |  |  | 130 |  |  |  |  | 135 |  |  |  |  | 140 |  |

432

| GCC | GTG | TTC | GCT | TTC | ATG | TGG | CTA | GTT | AGT | TCA | TCA | GCC | TGG | GCC | AAA |
|---|---|---|---|---|---|---|---|---|---|---|---|---|---|---|---|
| Ala | Val | Phe | Ala | Phe | Met | Trp | Leu | Val | Ser | Ser | Ser | Ala | Trp | Ala | Lys |
|  |  |  | 145 |  |  |  |  | 150 |  |  |  |  | 155 |  |  |

480

| GGC | CTG | TCC | GAT | GTG | AAG | ATG | GCC | ACG | GAC | CCA | GAG | AAC | ATT | ATC | AAG |
|---|---|---|---|---|---|---|---|---|---|---|---|---|---|---|---|
| Gly | Leu | Ser | Asp | Val | Lys | Met | Ala | Thr | Asp | Pro | Glu | Asn | Ile | Ile | Lys |
|  |  | 160 |  |  |  |  | 165 |  |  |  |  | 170 |  |  |  |

528

| GAG | ATG | CCC | ATG | TGC | CGC | CAG | ACA | GGG | AAC | ACA | TGC | AAG | GAA | CTG | AGG |
|---|---|---|---|---|---|---|---|---|---|---|---|---|---|---|---|
| Glu | Met | Pro | Met | Cys | Arg | Gln | Thr | Gly | Asn | Thr | Cys | Lys | Glu | Leu | Arg |
| 175 |  |  |  |  | 180 |  |  |  |  | 185 |  |  |  |  |  |

576

| GAC | CCT | GTG | ACT | TCA | GGA | CTC | AAC | ACC | TCA | GTG | GTG | TTT | GGC | TTC | CTG |
|---|---|---|---|---|---|---|---|---|---|---|---|---|---|---|---|
| Asp | Pro | Val | Thr | Ser | Gly | Leu | Asn | Thr | Ser | Val | Val | Phe | Gly | Phe | Leu |
| 190 |  |  |  |  | 195 |  |  |  |  | 200 |  |  |  |  | 205 |

624

| AAC | CTG | GTG | CTC | TGG | GTT | GGC | AAC | TTA | TGG | TTC | GTG | TTC | AAG | GAG | ACA |
|---|---|---|---|---|---|---|---|---|---|---|---|---|---|---|---|
| Asn | Leu | Val | Leu | Trp | Val | Gly | Asn | Leu | Trp | Phe | Val | Phe | Lys | Glu | Thr |
|  |  |  |  | 210 |  |  |  |  | 215 |  |  |  |  | 220 |  |

672

| GGC | TGG | GCA | GCC | CCA | TTC | ATG | CGC | GCA | CCT | CCA | GGC | GCC | CCG | GAA | AAG |
|---|---|---|---|---|---|---|---|---|---|---|---|---|---|---|---|
| Gly | Trp | Ala | Ala | Pro | Phe | Met | Arg | Ala | Pro | Pro | Gly | Ala | Pro | Glu | Lys |
|  |  |  | 225 |  |  |  |  | 230 |  |  |  |  | 235 |  |  |

720

| CAA | CCA | GCA | CCT | GGC | GAT | GCC | TAC | GGC | GAT | GCG | GGC | TAC | GGG | CAG | GGC |
|---|---|---|---|---|---|---|---|---|---|---|---|---|---|---|---|
| Gln | Pro | Ala | Pro | Gly | Asp | Ala | Tyr | Gly | Asp | Ala | Gly | Tyr | Gly | Gln | Gly |
|  |  | 240 |  |  |  |  | 245 |  |  |  |  | 250 |  |  |  |

768

| CCC | GGA | GGC | TAT | GGG | CCC | CAA | GAC | TCC | TAC | GGG | CCT | CAG | GGT | GGT | TAT |
|---|---|---|---|---|---|---|---|---|---|---|---|---|---|---|---|
| Pro | Gly | Gly | Tyr | Gly | Pro | Gln | Asp | Ser | Tyr | Gly | Pro | Gln | Gly | Gly | Tyr |
|  | 255 |  |  |  |  | 260 |  |  |  |  | 265 |  |  |  |  |

816

| CAA | CCC | GAT | TAC | GGG | CAG | CCA | GCC | AGC | GGT | GGC | GGT | GGC | TAC | GGG | CCT |
|---|---|---|---|---|---|---|---|---|---|---|---|---|---|---|---|
| Gln | Pro | Asp | Tyr | Gly | Gln | Pro | Ala | Ser | Gly | Gly | Gly | Gly | Tyr | Gly | Pro |
| 270 |  |  |  | 275 |  |  |  |  | 280 |  |  |  |  |  | 285 |

864

| CAG | GGC | GAC | TAT | GGG | CAG | CAA | GGC | TAT | GGC | CAA | CAG | GGT | GCG | CCC | ACC |
|---|---|---|---|---|---|---|---|---|---|---|---|---|---|---|---|
| Gln | Gly | Asp | Tyr | Gly | Gln | Gln | Gly | Tyr | Gly | Gln | Gln | Gly | Ala | Pro | Thr |
|  |  |  |  | 290 |  |  |  |  | 295 |  |  |  |  | 300 |  |

912

| TCC | TTC | TCC | AAT | CAG | ATG | TAATCTGGTC | AGTGAAGTTC | ATGAAGATCC |
|---|---|---|---|---|---|---|---|---|
| Ser | Phe | Ser | Asn | Gln | Met |  |  |  |
|  |  |  |  | 305 |  |  |  |  |

960

| CACGGGTGGG | CAAGAGCTCA | AGAGAAGGCC | TGCCCCCCTT | TTCCCATCCC | CATATCCTAG | 1020 |
|---|---|---|---|---|---|---|
| GCCTCCACCC | CTCAACCCAG | GAGACCCTAA | CTGTCTTTGC | TGTTTATATA | TATATATATT | 1080 |
| ATATATAAAT | ATCTATTTAT | CTGTCTGAGC | CCTACATTCA | CCCACTTCTC | CATGCACTAG | 1140 |
| AGGCCCAGTC | CTGAATGGGC | TCCTCCCCAA | CCCTGACCTT | GCATTCCTCA | GCCCCTATCT | 1200 |
| GTTCCCCAGC | CCTGTCCCTT | GAGGTAAGGG | GCTCTAGAAA | GGGGACAGGA | AGGGAACCAG | 1260 |
| ACCTTGGCTG | CATGGAGTGG | GTTGGTGTGA | CTTTCTCTCC | TTCCTCCTCT | CCCTCTGCCC | 1320 |
| CTCCTAACTC | TGGCCTTGGT | CCTCCAGCAT | CACCTGAACT | TCAGAAGCTC | TCGAATGGAA | 1380 |
| ATCTGACCCC | AAGAGTAGAG | CAGTAGACTG | AGTGGAGGAG | GCTTGGGTGA | AACGGGCAGA | 1440 |
| GAGGAGATAA | CCTCTGTAGA | GAGAGGACTA | GTCAGCCAAG | AGTTGAATTC | CAGACATACT | 1500 |
| GGATGTGCAG | TCTAAAAGGA | AAGTGGTATC | CTACCGCATT | CTGCAATGGG | GCTTTAAGTG | 1560 |

-continued

```
ACCAGAGAGA GTGGTTCTAG GAGGGGTGTG GCTTAAACAC AGCGGGCTCC AGAGTGGGCA    1620
GGTTTGGGTT GGATCCAGCA TCTCTAGAAG GGGTGTGTCT TGGAACATTC AGGAGTTTGA    1680
GCTTGATTCC AAAGAGCTTG AGCAAGGGTA GAAGTGGGGT TCAGGGATGA TCTAAGCTTG    1740
AGATGAGGTC CTGCTTAGGA TTCCAGACAA GCATATGAAG AGATGTGTGG TGGTCTCAGA    1800
AGAGGAAACC CATTCTGTAA TGGGGCTGAG AAGAAAACAC GTTTTCAATT GAGTGGAGTT    1860
TGAGAGGGTG CAGGAGGCCA TGGTTAGGAG CTATGAGGTG AGTTTGCTA  AAAGCAGGAG    1920
GGCGTACTCC                                                           1930
```

( 2 ) INFORMATION FOR SEQ ID NO: 2:

( i ) SEQUENCE CHARACTERISTICS:
        ( A ) LENGTH: 307 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met Asp Val Val Asn Gln Leu Val Ala Gly Gly Gln Phe Arg Val Val
 1               5                  10                  15

Lys Glu Pro Leu Gly Phe Val Lys Val Leu Gln Trp Val Phe Ala Ile
                20                  25                  30

Phe Ala Phe Ala Thr Cys Gly Ser Tyr Thr Gly Glu Leu Arg Leu Ser
            35                  40                  45

Val Glu Cys Ala Asn Lys Thr Glu Ser Ala Leu Asn Ile Glu Val Glu
     50                  55                  60

Phe Glu Tyr Pro Phe Arg Leu His Gln Val Tyr Phe Asp Ala Pro Ser
 65                  70                  75                  80

Cys Val Lys Gly Gly Thr Thr Lys Ile Phe Leu Val Gly Asp Tyr Ser
                 85                  90                  95

Ser Ala Glu Phe Phe Val Thr Val Ala Val Phe Ala Phe Leu Tyr
                100                 105                 110

Ser Met Gly Ala Leu Ala Thr Tyr Ile Phe Leu Gln Asn Lys Tyr Arg
            115                 120                 125

Glu Asn Asn Lys Gly Pro Met Met Asp Phe Leu Ala Thr Ala Val Phe
    130                 135                 140

Ala Phe Met Trp Leu Val Ser Ser Ser Ala Trp Ala Lys Gly Leu Ser
145                 150                 155                 160

Asp Val Lys Met Ala Thr Asp Pro Glu Asn Ile Ile Lys Glu Met Pro
                165                 170                 175

Met Cys Arg Gln Thr Gly Asn Thr Cys Lys Glu Leu Arg Asp Pro Val
            180                 185                 190

Thr Ser Gly Leu Asn Thr Ser Val Val Phe Gly Phe Leu Asn Leu Val
    195                 200                 205

Leu Trp Val Gly Asn Leu Trp Phe Val Phe Lys Glu Thr Gly Trp Ala
210                 215                 220

Ala Pro Phe Met Arg Ala Pro Pro Gly Ala Pro Glu Lys Gln Pro Ala
225                 230                 235                 240

Pro Gly Asp Ala Tyr Gly Asp Ala Gly Tyr Gly Gln Gly Pro Gly Gly
                245                 250                 255

Tyr Gly Pro Gln Asp Ser Tyr Gly Pro Gln Gly Gly Tyr Gln Pro Asp
            260                 265                 270

Tyr Gly Gln Pro Ala Ser Gly Gly Gly Gly Tyr Gly Pro Gln Gly Asp
    275                 280                 285

Tyr Gly Gln Gln Gly Tyr Gly Gln Gln Gly Ala Pro Thr Ser Phe Ser
290                 295                 300
```

Asn Gln Met
305

METHOD OF SCREENING FOR SMALL CELL LUNG CARCINOMA

This application is a continuation-in-part of application Ser. No. 07/617,102 filed Nov. 21, 1990, now abandoned.

DESCRIPTION

The invention concerns a method for the detection of a small cell lung carcinoma by determination of synaptophysin.

Malignant tumours of the lung and the respiratory system are particularly common among cancers and spread by invasive growth both regionally as well as by distant metastasis. In this connection a clinical distinction is made between four different major types of tumours i.e. the small cell lung carcinoma (SCLC), the epithelioma squamous cell carcinoma, the adenocarcinoma and the large cell anaplastic carcinoma whereby the latter three types are usually combined under the heading "non small cell carcinomas". Since small cell lung carcinomas on the one hand metastasise particularly early and in addition exhibit a particularly fast tumour growth, but on the other hand, are very sensitive to radiotherapy and chemotherapy compared to the non small cell lung carcinomas, an early recognition of this tumour and its differentiation from other types of tumours is crucial for the prognosis of this disease.

It was therefore the object of the invention to provide a test for the occurrence of small cell lung carcinomas without having to remove tissue specimens from patients.

This object is achieved according to the present invention by determining synaptophysin, its oligomers and/or its fragments in body fluids. Surprisingly, it was found that the protein synaptophysin, which is usually bound strongly to the membrane, its oligomers and/or its immunologically detectable fragments, can be detected in body fluids of patients with small cell lung carcinoma.

Synaptophysin which possibly plays an important role in the regulation, the storage and/or the release of neurotransmitters has already been the subject of intensive investigations. From R. Leube et al., EMBO Journal, Vol. 6 (1987), 3261-3268 it is already known that different types of human small cell lung carcinomas can be characterized by the appearance of synaptophysin mRNA. The synaptophysin itself, which is an N-glycosylated protein, is usually found in neurosecretory vesicles, in particular in presynaptic vesicles as well as in vesicles of different neuroendocrine cells both of the neuronal as well as the epithelial phenotype. The amino acid sequence of this protein and the nucleotide sequence of its respective mRNA is known for human as well as for rat cells e.g. from T. Südhof et al., Nucleic Acids Research, Vol. 15, No. 22 (1987), 9607 as well as from T. Südhof et al., Science, Vol. 238 (1987), 1142–1144 as well as from the literature reference of R. Leube et al., mentioned above. Accordingly synaptophysin is a protein integrated into the vesicle membrane which penetrates the vesicle membrane four times over its entire length in a thread-like manner (Science 238 (1987) 1142–1144, Science 242 (1988) 1050–1052). Furthermore, monoclonal antibodies are already known which are directed against sequences of the 89 carboxy-terminal amino acids in particular of rat synaptophysin.

In the method according to the present invention serum is preferably used as the body fluid. Other body fluids such as pulmonary secretions, lymph or saliva can, however, also be used for carrying out the method according to the present invention. The determination of the synaptophysin in the body fluid is carried out in a manner known to the expert. The synaptophysin is, however, preferably detected using immunological methods. It has proven expedient to use antibodies (polyclonal or monoclonal antibodies as antisera) for this which are directed against the sequences of the synaptophysin protruding from the vesicle membrane. It is expedient to use antigenic determinants for the formation of the antibodies whose amino acid sequences are derived from human or rat synaptophysin. Particularly effective epitopes which are suitable for the formation of the antibodies used in the method according to the present invention are composed of the amino acid sequences which are at the carboxy-terminal end of the synaptophysin molecule. These are, in particular, the 89 amino acids at the carboxy-terminal end of rat synaptophysin (amino acids 219–307) and the corresponding sequence which is 90 amino acids long of human synaptophysin (amino acids 207–296).

Antibodies which are directed against the translation product of the clone fragment of pSR[1] or against fragments thereof have also proven to be particularly suitable for the method according to the present invention. The production of the clone fragment pSR[1] is known and is e.g. described in Synaptophysin: Molecular Organisation and mRNA-expression as determined from cloned cDNA, EMBO Journal, Vol. 6, No. 11, (1987), p. 3261-3268 by R. E. Leube et al.

Monoclonal as well as polyclonal antibodies are suitable for carrying out the method according to the present invention whereby, however, monoclonal antibodies are preferred. It has proven particularly expedient to use the MAB SY38 (Cell 41 (1985) 1017–1028) to carry out the method according to the present invention which can be obtained from the cell line which is deposited at the ECACC under the number 89112801. accepted by the European Collection of Animal Cell Cultures, PHLS CAMR, Porton Down, Salisbury, Wiltshire, SP4 OIG, U.K. on Nov. 28, 1989.

Apart from the antibodies themselves, antibody fragments which contain the hypervariable regions such as e.g. the Fab or F(ab')₂ fragments can, however, also be used in the method according to the present invention. These fragments are preferably present in an immobilized form bound on a carrier and are particularly suitable for carrying out enzyme-immunoassays or radioimmunoassays.

Usually the determination of synaptophysin in serum is carried out in such a way that 1. a synaptophysin antibody which is preferably a MAB is bound to a carrier, usually a microtitre plate,
2. subsequently it is incubated with the sample whereby the antigen to be determined is bound to the antibody or its fragments;
3. the bound antigen is incubated with a synaptophysin antibody which is usually identical but labelled and
4. a detection reaction is carried out using a chromogenic substrate and
5. the absorbance of the chromogenic substrate is measured photometrically.

It has proven to be advantageous to bind the antibody either directly to the carrier when carrying out the first step of the method or it is immobilized in another way known to the expert for example as a biotin-conjugate on a plate coated with streptavidin or avidin. When carrying out the third step of the method it is also possible to use an antibody as detector AB which recognises a different epitope on the synaptophysin than the AB of the first step of the procedure. It is also possible according to the present invention to carry out the labelling by means of radioactive, fluorescent or chemiluminescent substances. Enzymes which are suitable for such labelling are known to the expert. Peroxidase, alkaline phosphatase and β-galactosidase have, however, proven to be particularly suitable.

The invention is elucidated further by the following Examples.

EXAMPLE 1

Detection of synaptophysin

The wells of a microtitre plate (Nunc company) are coated for one hour at room temperature with 2 μg/ml MAB SY38 in bicarbonate buffer, pH 9.6. They are washed three times with 0.05 % Tween 20/PBS (8 g/l NaCl, 0.2 g/l KCl, 1.44 g/l $Na_2HPO_4 \times 2H_2O$, 0.2 g/l $KH_2PO_4$) and re-coated for one hour at room temperature with 2% ovalbumin/PBS (phosphate buffered saline). Subsequently they are washed three times with 0.05% Tween ® in PBS.

The sample to be determined is added diluted in PBS. It is incubated for 1.5 hours at room temperature and washed four times with 0.05% Tween. Subsequently a solution of a conjugate of MAB SY38 to peroxidase (peroxidase activity 150 μ/ml) is added, incubated for 1.5 hours at room temperature and washed three times with 0.05% Tween PBS.

The peroxidase activity is determined via the ABTS ® colour reaction after addition of a solution of 1.9 mmol/l ABTS ® (2,2'-azino-di[3-ethyl-benzthiazolinesulphonic acid (6)]-diammonium salt, 100 mmol/l phosphate/citrate buffer, pH 4.4, 3.2 mmol/l sodium perborate) and the absorbance is measured at 405 nm as a measure for the analyte concentration.

EXAMPLE 2

Sera from 52 patients were examined using a microtitre plate produced according to Example 1. The result of this examination can be seen in the following Table 1.

TABLE 1

|  | positive | examined |
|---|---|---|
| 1. healthy | 0 | 7 |
| 2. benign diseases | 1 | 15 |
| 3. carcinomas | | |
| 3.1.bronchial carcinomas: | | |
| non-SCLC | 1 | 4 |
| SCLC | 6 | 11 |
| 3.2.other carcinomas | 1 | 15 |

---

We claim:

1. A method of screening for small cell lung carcinoma comprising,
  contacting a body fluid sample with antibodies or antibody fragments which specifically bind synaptophysin,
  detecting at least one member of the group consisting of synaptophysin monomers, synaptophysin oligomers, and synaptophysin fragments,
  wherein the presence of synaptophysin in the body fluid sample is associated with the presence of small cell lung carcinoma.

2. The method according to claim 1, wherein said body fluid sample is serum.

3. The method according to claim 1, wherein said antibodies or antibody fragments specifically bind synaptophysin sequences which protrude from a vesicle membrane.

4. The method according to claim 3, wherein said antibodies are directed against a carboxy-terminal end of said synaptophysin.

5. The method according to claim 3 wherein antibodies directed against a translation product of a clone fragment pSR$^1$ or fragments thereof are used to detect said synaptophysin.

6. The method according to claim 3 wherein said antibodies are directed against an amino acid sequence 207 to 296 of a carboxy-terminal end of human synaptophysin.

7. The method according to claim 3 wherein said antibodies are directed against an amino acid sequence 219–307 of a carboxy-terminal end of rat synaptophysin.

8. The method according to claim 3, wherein said antibodies are directed against a 90 amino acid portion of a carboxy-terminal end of human synaptophysin.

9. The method according to claim 8, wherein said 90 amino acid portion is the last 90 amino acids of said carboxy terminal end.

10. The method according to claim 3, wherein said antibodies are monoclonal antibody SY38 derived from cell line ECACC 89112801.

11. The method according to claim 3 wherein said antibodies are fragments of antibodies.

12. The method according to claim 11, wherein said fragments of antibodies are Fab and/or F(ab')$_2$.

13. A method of screening for small cell lung carcinoma comprising,
  contacting a serum sample with antibodies or antibody fragments which specifically bind synaptophysin,
  detecting at least one member of the group consisting of synaptophysin monomers, synaptophysin oligomers, and synaptophysin fragments,
  wherein the presence of synaptophysin in the serum sample is associated with the presence of small cell lung carcinoma.

14. The method according to claim 13, wherein said antibodies or antibody fragments specifically bind synaptophysin sequences which protrude from a vesicle membrane.

15. The method according to claim 14, wherein said antibodies are directed against a carboxy-terminal end of said synaptophysin.

16. The method according to claim 14 wherein antibodies directed against a translation product of a clone fragment pSR$^1$ or fragments thereof are used to detect said synaptophysin.

17. The method according to claim 14 wherein said antibodies are directed against an amino acid sequence 207 to 296 of a carboxy-terminal end of human synaptophysin.

18. The method according to claim 14 wherein said antibodies are directed against an amino acid sequence 219–307 of a carboxy-terminal end of rat synaptophysin.

19. The method according to claim 14, wherein said antibodies are directed against a 90 amino acid portion of a carboxy-terminal end of human synaptophysin.

20. The method according to claim 14, wherein said 90 amino acid portion is the last 90 amino acids of said carboxy terminal end.

21. The method according to claim 14, wherein said antibodies are monoclonal antibody SY38 derived from cell line ECACC 89112801.

22. The method according to claim 14 wherein said antibodies are fragments of antibodies.

23. The method according to claim 22, wherein said fragments of antibodies are Fab and/or F(ab')$_2$.

* * * * *